(12) United States Patent
Peters

(10) Patent No.: US 9,427,605 B2
(45) Date of Patent: Aug. 30, 2016

(54) COSMETIC TREATMENT WITH NITRIC OXIDE, DEVICE FOR PERFORMING SAID TREATMENT AND MANUFACTURING METHOD THEREFOR

(75) Inventor: Tor Peters, Helsingborg (SE)

(73) Assignee: Novan, Inc., Durham, NC (US)

( * ) Notice: Subject to any disclaimer, the term of this patent is extended or adjusted under 35 U.S.C. 154(b) by 2461 days.

(21) Appl. No.: 11/909,152

(22) PCT Filed: Feb. 13, 2006

(86) PCT No.: PCT/EP2006/050884
§ 371 (c)(1),
(2), (4) Date: Apr. 30, 2008

(87) PCT Pub. No.: WO2006/100154
PCT Pub. Date: Sep. 28, 2006

(65) Prior Publication Data
US 2008/0311163 A1   Dec. 18, 2008

Related U.S. Application Data

(60) Provisional application No. 60/666,504, filed on Mar. 30, 2005, provisional application No. 60/711,006, filed on Aug. 24, 2005.

(30) Foreign Application Priority Data

Mar. 24, 2005 (EP) .................................. 05006474
Aug. 23, 2005 (EP) .................................. 05018269

(51) Int. Cl.
*A61K 8/19* (2006.01)
*A61K 8/84* (2006.01)
(Continued)

(52) U.S. Cl.
CPC ............. *A61Q 19/00* (2013.01); *A61K 8/0208* (2013.01); *A61K 8/19* (2013.01); *A61K 8/84* (2013.01);
(Continued)

(58) Field of Classification Search
CPC .. A61K 2800/54; A61K 8/0208; A61K 8/19; A61K 8/84; A61L 15/44; A61L 2300/114; A61L 2300/602; A61Q 19/00; A61Q 19/06; A61Q 19/08
See application file for complete search history.

(56) References Cited

U.S. PATENT DOCUMENTS 3,754,368 A   8/1973   Moore et al.
4,182,827 A   1/1980   Jones et al.
(Continued)

FOREIGN PATENT DOCUMENTS

CA   2 594 407 A1   8/2006
EP   1 300 424 A1   4/2003
(Continued)

OTHER PUBLICATIONS

Al-Sa'doni et al. (clinical science 2000, 98, 507-520).*
(Continued)

*Primary Examiner* — Ernst V Arnold
(74) *Attorney, Agent, or Firm* — Myers Bigel & Sibley, P.A.

(57) ABSTRACT

A cosmetic treatment device includes a nitric oxide (NO) eluting polymer, a carrier, and a proton donor enclosed in a container that keeps the proton donor separate from the nitric oxide eluting polymer until the device is used. When the container is opened, proton donor contacts the polymer, causing the elution of nitric oxide from the polymer.

26 Claims, 4 Drawing Sheets

(51) Int. Cl.
  *A61L 15/44* (2006.01)
  *A61Q 19/00* (2006.01)
  *A61Q 19/06* (2006.01)
  *A61Q 19/08* (2006.01)
  *A61K 8/02* (2006.01)

(52) U.S. Cl.
  CPC ............... *A61L 15/44* (2013.01); *A61Q 19/06* (2013.01); *A61Q 19/08* (2013.01); *A61K 2800/54* (2013.01); *A61L 2300/114* (2013.01); *A61L 2300/602* (2013.01)

(56) References Cited

U.S. PATENT DOCUMENTS

| | | |
|---|---|---|
| 4,829,092 A | 5/1989 | Nelson et al. |
| 4,917,886 A | 4/1990 | Asche et al. |
| 5,405,919 A | 4/1995 | Keefer |
| 5,519,020 A | 5/1996 | Smith et al. |
| 5,691,423 A | 11/1997 | Smith et al. |
| 5,770,645 A | 6/1998 | Stamler et al. |
| 5,814,656 A | 9/1998 | Saavedra et al. |
| 5,814,666 A | 9/1998 | Green et al. |
| 5,840,759 A * | 11/1998 | Mitchell et al. ............... 424/718 |
| 5,910,316 A | 6/1999 | Keefer et al. |
| 5,958,427 A | 9/1999 | Salzman et al. |
| 5,968,528 A | 10/1999 | Deckner et al. |
| 6,103,266 A | 8/2000 | Tapolsky et al. |
| 6,103,275 A | 8/2000 | Seitz et al. |
| 6,110,453 A | 8/2000 | Keefer et al. |
| 6,303,141 B1 | 10/2001 | Fischer et al. |
| 6,382,526 B1 | 5/2002 | Reneker et al. |
| 6,465,445 B1 | 10/2002 | Labrie |
| 6,520,425 B1 | 2/2003 | Reneker |
| 6,695,992 B2 | 2/2004 | Reneker |
| 6,737,447 B1 | 5/2004 | Smith et al. |
| 6,818,018 B1 | 11/2004 | Sawhney |
| 6,861,064 B1 | 3/2005 | Laakso et al. |
| 7,048,951 B1 * | 5/2006 | Seitz et al. .................... 424/718 |
| 7,704,518 B2 | 4/2010 | Tamarkin et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,486,451 B2 | 7/2013 | Morris et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,722,103 B2 | 5/2014 | Morris et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,265,725 B2 | 2/2016 | Tamarkin et al. |
| 9,320,705 B2 | 4/2016 | Tamarkin et al. |
| 2002/0012816 A1 | 1/2002 | Shimizu et al. |
| 2002/0013304 A1 | 1/2002 | Wilson et al. |
| 2002/0028223 A1 | 3/2002 | Vatter et al. |
| 2002/0082221 A1 * | 6/2002 | Herrmann et al. ............. 514/23 |
| 2002/0094985 A1 | 7/2002 | Herrmann et al. |
| 2002/0122771 A1 | 9/2002 | Holland et al. |
| 2002/0136750 A1 | 9/2002 | Benjamin et al. |
| 2002/0155174 A1 | 10/2002 | Benjamin et al. |
| 2003/0077243 A1 | 4/2003 | Fitzhugh |
| 2003/0159702 A1 | 8/2003 | Lindell et al. |
| 2003/0175328 A1 | 9/2003 | Shefer et al. |
| 2003/0205234 A1 | 11/2003 | Bardach et al. |
| 2003/0235605 A1 | 12/2003 | Lelah et al. |
| 2004/0009238 A1 | 1/2004 | Miller et al. |
| 2004/0043068 A1 | 3/2004 | Tedeschi et al. |
| 2004/0068005 A1 | 4/2004 | Szilvassy et al. |
| 2004/0171589 A1 | 9/2004 | Herrmann et al. |
| 2004/0202684 A1 | 10/2004 | Djerassi |
| 2004/0220260 A1 | 11/2004 | Cals-Grierson |
| 2004/0265244 A1 | 12/2004 | Rosen |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0160897 A1 | 7/2006 | Pelicci et al. |
| 2006/0173076 A1 | 8/2006 | Vishnupad et al. |
| 2006/0269620 A1 | 11/2006 | Morris et al. |
| 2006/0275218 A1 | 12/2006 | Tamarkin et al. |
| 2007/0166255 A1 | 7/2007 | Gupta |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0071206 A1 | 3/2008 | Peters |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0068248 A1 | 3/2009 | Waterhouse et al. |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2009/0226380 A1 | 9/2009 | Clark et al. |
| 2009/0297634 A1 | 12/2009 | Friedman et al. |
| 2010/0015253 A1 | 1/2010 | Benjamin |
| 2010/0098733 A1 | 4/2010 | Stasko |
| 2010/0221195 A1 | 9/2010 | Tamarkin et al. |
| 2010/0266510 A1 | 10/2010 | Tamarkin et al. |
| 2010/0286285 A1 | 11/2010 | Barthez et al. |
| 2010/0310476 A1 | 12/2010 | Tamarkin et al. |
| 2010/0331968 A1 | 12/2010 | Morris et al. |
| 2011/0027369 A1 | 2/2011 | Franke |
| 2011/0045037 A1 | 2/2011 | Tamarkin et al. |
| 2011/0052650 A1 | 3/2011 | Morris et al. |
| 2011/0082167 A1 | 4/2011 | Pisak et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2012/0114547 A1 | 5/2012 | Smith |
| 2012/0134951 A1 | 5/2012 | Stasko et al. |
| 2012/0136323 A1 | 5/2012 | Stasko et al. |
| 2012/0141384 A1 | 6/2012 | Tamarkin et al. |
| 2012/0156163 A1 | 6/2012 | Bauman et al. |
| 2012/0237453 A1 | 9/2012 | Tamarkin et al. |
| 2013/0059017 A1 | 3/2013 | Perricone et al. |
| 2013/0109756 A1 | 5/2013 | Huber et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0017121 A1 | 1/2014 | Schoenfisch et al. |
| 2014/0057001 A1 | 2/2014 | Bauman et al. |
| 2014/0058124 A1 | 2/2014 | Schoenfisch et al. |
| 2014/0065200 A1 | 3/2014 | Schoenfisch et al. |
| 2014/0107071 A1 | 4/2014 | Kougoulos et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |

(56) References Cited

U.S. PATENT DOCUMENTS

| | | |
|---|---|---|
| 2015/0111973 A1 | 4/2015 | Bauman et al. |
| 2015/0118164 A1 | 4/2015 | Tamarkin et al. |
| 2015/0141606 A1 | 5/2015 | Bao et al. |
| 2015/0182543 A1 | 7/2015 | Schoenfisch et al. |
| 2015/0225488 A1 | 8/2015 | Schoenfisch et al. |
| 2016/0008275 A1 | 1/2016 | Doxey et al. |

FOREIGN PATENT DOCUMENTS

| | | |
|---|---|---|
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| GB | 2 354 441 | 3/2001 |
| WO | WO 93/10754 A1 | 6/1993 |
| WO | WO 96/13164 A1 | 5/1996 |
| WO | WO 96/15797 A1 | 5/1996 |
| WO | WO 98/05689 A1 | 2/1998 |
| WO | WO 00/49993 A2 | 8/2000 |
| WO | WO 01/26702 A2 | 4/2001 |
| WO | WO 01/85013 A2 | 11/2001 |
| WO | WO 02/20026 A2 | 3/2002 |
| WO | WO 02/056864 A2 | 7/2002 |
| WO | WO 03/013489 A1 | 2/2003 |
| WO | WO 03/072039 A2 | 9/2003 |
| WO | WO 03/078437 A1 | 9/2003 |
| WO | WO 03/086282 A2 | 10/2003 |
| WO | WO 03/092763 A1 | 11/2003 |
| WO | WO 2004/012659 A2 | 2/2004 |
| WO | WO 2004/012874 A1 | 2/2004 |
| WO | WO 2004/098538 A2 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/037339 A1 | 4/2005 |
| WO | WO 2005/046661 A2 | 5/2005 |
| WO | WO 2006/084910 A2 | 8/2006 |
| WO | WO 2006/084912 A1 | 8/2006 |
| WO | WO 2006/100154 A1 | 9/2006 |
| WO | WO 2006/128121 A2 | 11/2006 |
| WO | WO 2006/138035 A1 | 12/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2011/005846 A1 | 1/2011 |
| WO | WO 2011/022652 A1 | 2/2011 |
| WO | WO 2011/022680 A2 | 2/2011 |
| WO | WO 2011/061519 A2 | 5/2011 |
| WO | WO 2012/100174 A1 | 7/2012 |
| WO | WO 2012/153331 A2 | 11/2012 |
| WO | WO 2013/006608 A1 | 1/2013 |
| WO | WO 2013/006613 A1 | 1/2013 |
| WO | WO 2013/138073 A1 | 9/2013 |
| WO | WO 2013/138075 A1 | 9/2013 |
| WO | WO 2015/021382 A2 | 2/2015 |
| WO | WO 2016/007834 A1 | 1/2016 |
| WO | WO 2016/010988 A1 | 1/2016 |
| WO | WO 2016/022170 A1 | 2/2016 |

OTHER PUBLICATIONS

Wang et al. Chemical Reviews 2002, 102(4), 1091-1134).*
Hrabie et al. Chem Rev 2002, 102, 1135-1154).*
U.S. Appl. No. 14/133,973, Kougoulos et al., filed Dec. 19, 2013.
U.S. Appl. No. 14/191,958, Doxey, filed Feb. 27, 2014.
U.S. Appl. No. 14/771,138, Doxey, filed Aug. 27, 2015.
Amadeu et al. "Nitric Oxide Donor Improves Healing if Applied on Inflammatory and Proliferative Phase" *Journal of Surgical Research* 149:84-93 (2008).
Bohl Masters et al. "Effects of nitric oxide releasing poly(vinyl alcohol) hydrogel dressings on dermal wound healing in diabetic mice" *Wound Repair and Regeneration* 10(5):286-294 (2002).
Hetrick et al. "Anti-biofilm efficacy of nitric oxide-releasing silica nanoparticles" *Biomaterials* 30:2782-2789 (2009).
Pulfer et al. "Incorporation of nitric oxide-releasing crosslinked polyethyleneimine microspheres into vascular grafts" *Journal of Biomedical Materials Research* 37:182-189 (1997).
Sangster, James "Octanol-Water Partition Coefficients of Simple Organic Compounds" *Journal of Physical and Chemical Reference Data* 18(3):1111-1227 (1989).
Smith et al. "Transdermal delivery of nitric oxide from diazeniumdiolates" *Journal of Controlled Release* 51:153-159 (1998).
Boykin et al. "HBO Mediates Increased Nitric Oxide Production Associated With Wound Healing" *Wound Repaid and Regeneration* 12(2):A15 (Abstract 054) (2004).

* cited by examiner

COSMETIC TREATMENT WITH NITRIC OXIDE, DEVICE FOR PERFORMING SAID TREATMENT AND MANUFACTURING METHOD THEREFOR

RELATED APPLICATIONS

This application claims priority to International Patent Application Number PCT/EP2006/050884, international filing date 13 Feb. 2006, entitled "Cosmetic Treatment With Nitric Oxide, Device For Performing Said Treatment And Manufacturing Method Therefor," which claims priority to European Patent Application No. 05006474.0 filed 24 Mar. 2005 entitled "Cosmetic Treatment With Nitric Oxide, Device For Performing Said Treatment And Manufacturing Method Therefor," U.S. Provisional Application Ser. No. 60/666,504 filed Mar. 30, 2005 entitled "Cosmetic Treatment With Nitric Oxide, Device For Performing Said Treatment And Manufacturing Method Therefor," European Patent Application No. 05018269.0 filed 23 Aug. 2005 entitled "Device, System, And Method Comprising Microencapsulated Liquid For Release Of Nitric Oxide From A Polymer," and U.S. Provisional Application Ser. No. 60/711,006 filed Aug. 24, 2005 entitled "Device, System, And Method Comprising Microencapsulated Liquid For Release Of Nitric Oxide From A Polymer," all of which are hereby incorporated by reference.

FIELD OF THE INVENTION

This invention pertains in general to the field of cosmetic treatment, involving the use of nitric oxide (NO). More particularly the invention relates to a device for performing said treatment, and a process for manufacturing of said device, involving the use of nitric oxide (NO) for cosmetic purposes.

BACKGROUND OF THE INVENTION

In the society of today there is an increasing demand for products that will improve the physiological visual appearance of human beings.

Chronological age, environmental factors, changes in physiological functions of skin, psoriasis, dermatitis, cellulites, viral and/or bacteriological attacks, are some factors that affect the appearance of human beings in a cosmetically undesirable way.

Many of the alterations mentioned above are caused by changes in the outer epidermal layer of the skin, while others are caused by changes in the lower part of dermis. For instance, chronological age and extensive exposure to environmental factors, such as sun radiation, affect dermis in such way that dermis undergoes structural and functional changes, which result in many of the characteristics of aged skin, such as loss of elasticity, formation of wrinkles, loss of water-holding capacity, uneven distribution of fat, cellulites and sagging.

One thing that these factors have in common is that they are obtained by the loss of blood perfusion in the affected tissues.

Viral and bacteriological attacks may also result in impaired cosmetic appearance. Examples of such viral or bacteriological attack are herpes, such as Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, genital warts or warts, such as verruca vulgaris, verruca planae, verruca seborroica, filiform warts, mosaic warts, etc., caused by virus, and molluscs, caused by poxvirus. Such attacks lead often to cosmetically unaccepted skin defects, such as scars.

Psoriasis, such as invers psoriasis, psoriasis guttata, psoriasis pustulosa etc., is an inflammatory reaction in the skin, that may appear as a consequence of infection of *Streptococcus*. The disorder is not a self-healing disorder, and has to be treated, if the person suffering from psoriasis finds the disorder disfiguring or affecting his/her appearance in an undesirable way. Treatment of psoriasis is restricted to anti-inflammatory substances, such as glucocorticosteroids. This kind of treatment is often accompanied by adverse side effects, such as skin atrophy, telangiectasia, striae, hypertrichosis, rosacea, and dermatitis.

Dermatitis is another skin disorder that may disfigure a person, or affect the visual appearance of the person in a negative way.

The techniques according to the prior art, in respect of chronological age, environmental factors, changes in physiological functions of skin, include numerous of physiological, chemical, and mechanical methods, such as treatment with hydroxy acids, retinoids, barrier disrupters, tape stripping, solvent extraction etc. These methods present various drawbacks, such as irritation of the skin, skin toxicity, the requirement of high concentrations of expensive ingredients, pH values that are incompatible with the optimum pH value of the skin, long and cumbersome trials to establish whether or not a specific compound or composition is toxic or not, etc. Furthermore, the majority of the cosmetic methods according to the prior art induce invocation of damage of the skin, which results in the in set of repair mechanisms. Hence, there will be a period of time, such as weeks or months, during which the skin will remain irritated, and after which tolerance sets in and the irritations will diminish.

Up to this point there is no method, composition, compound etc., with the ability to simultaneously treat and prevent cosmetically undesirable disorders originating from both physiological factors, such as chronological age, environmental factors, changes in physiological functions of skin, such as psoriasis, dermatitis, cellulites, etc., and viral and bacteriological attacks.

Nitric oxide (NO) is a highly reactive molecule that is involved in many cell functions. In fact, nitric oxide plays a crucial role in the immune system and is utilized as an effector molecule by macrophages to protect itself against a number of pathogens, such as fungi, viruses, bacteria etc., and general microbial invasion. This improvement of healing is partly caused by NO inhibiting the activation or aggregation of blood platelets, and also by NO causing a reduction of inflammatory processes at the site of an implant.

NO is also known to have an anti-pathogenic, especially an anti-viral, effect, and furthermore NO has an anti-cancerous effect, as it is cytotoxic and cytostatic in suitable concentrations, i.e. it has among other effects tumoricidal and bacteriocidal effects. NO has for instance cytotoxic effects on human haematological malignant cells from patients with leukaemia or lymphoma, whereby NO may be used as a chemotherapeutic agent for treating such haematological disorders, even when the cells have become resistant to conventional anti-cancer drugs. This anti-pathogenic and anti-tumour effect of NO is taken advantage of by the present invention for cosmetic purposes, without having adverse effects.

However, due to the short half-life of NO, it has hitherto been very hard to treat viral, bacteria, virus, fungi or yeast infections with NO. This is because NO is actually toxic in high concentrations and has negative effects when applied in too large amounts to the body.

NO is actually also a vasodilator, and too large amounts of NO cause for instance a complete collapse of the circulatory system. On the other hand, NO has a very short half-life of fractions of a second up to a few seconds, once it is released. Hence, administration limitations due to short half-life and toxicity of NO have been limiting factors in the use of NO in the field of anti-pathogenic and anti-cancerous treatment so far.

In recent years research has been directed to polymers with the capability of releasing nitrogen oxide when getting in contact with water. Such polymers are for example polyalkyleneimines, such as L-PEI (Linear PolyEthylenelmine) and B-PEI (Branched PolyEthylenelmine), which polymers have the advantage of being biocompatible with natural products, after the release of nitrogen oxide.

Other example for NO eluting polymers are given in U.S. Pat. No. 5,770,645, wherein polymers derivatized with at least one $—NO_x$ group per 1200 atomic mass unit of the polymer are disclosed, X being one or two. One example is an S-nitrosylated polymer and is prepared by reacting a polythiolated polymer with a nitrosylating agent under conditions suitable for nitrosylating free thiol groups.

Akron University has developed NO-eluting L-PEI molecule that can be nano-spun onto the surface of medical devices to be permanently implanted in the body, such as implanted grafts, showing significant improvement of the healing process and reduced inflammation when implanting such devices. According to U.S. Pat. No. 6,737,447, a coating for medical devices provides nitric oxide delivery using nanofibers of linear poly (ethylenimine)-diazeniumdiolate. Linear poly (ethylenimine) diazeniumdiolate releases nitric oxide (NO) in a controlled manner to tissues and organs to aid the healing process and to prevent injury to tissues at risk of injury.

However, the meaning of "controlled" in the context of U.S. Pat. No. 6,737,447 is only directed to the fact that nitric oxide is eluted from the coating during a period of time. Therefore, the interpretation of "controlled" in respect of U.S. Pat. No. 6,737,447 is different from the meaning of "regulating" in the present invention. "Regulate", according to the present invention is intended to be interpreted as the possibility to vary the elution of nitric oxide to thereby achieve different elution profiles.

Electrospun nano-fibers of linear poly (ethylenimine) diazeniumdiolate deliver therapeutic levels of NO for cosmetic purposes to the tissues surrounding a medical device while minimizing the alteration of the properties of the device. A nanofiber coating, because of the small size and large surface area per unit mass of the nanofibers, provides a much larger surface area per unit mass while minimizing changes in other properties of the device.

However, the disclosure is both silent concerning an improvement of present technology in respect of cosmetic treatment of physiologically factors, disorders, such as psoriasis and dermatitis, and viral and/or bacteriological attacks, by the use of NO.

Hence, an improved, and more advantageous, method and device for the treatment and/or prevention of cosmetic disorders is desired. These cosmetic disorders comprise cosmetic disorders, which are caused by chronological age, environmental factors, changes in physiological functions of skin, psoriasis, dermatitis, cellulites, viral and/or bacteriological attacks. It is desired that the method and device do not develop resistance against the active pharmaceutical substance, and which preferably during the cosmetical treatment does not cause or causes minimal local skin irritation or contact allergic reactions, skin toxicity, the requirement of high concentrations of expensive ingredients, pH values that are incompatible with the optimum pH value of the skin, long and cumbersome trials to establish whether or not a specific compound or composition is toxic or not, skin atrophy, telangiectasia, striae, hypertrichosis, rosacea, dermatitis etc, would be advantageous, and in particular a method and device allowing for target improvement of the visual appearance would be advantageous.

OBJECTS AND SUMMARY OF THE INVENTION

Accordingly, the present invention preferably seeks to mitigate, alleviate or eliminate one or more of the above-identified deficiencies in the art and disadvantages singly or in any combination and solves, among others, the problems mentioned above, by providing an advantageous cosmetic treatment, a device for said cosmetic treatment, a manufacturing method for the latter and a use of nitric oxide according to the appended patent claims.

According to one aspect of the invention, a cosmetic treatment is provided that allows for target treatment of cosmetic disorders, caused by chronological age, environmental factors, changes in physiological functions of skin, such as psoriasis, dermatitis, cellulites, and viral and/or bacteriological attacks, for example herpes, such as Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, warts, such as verruca vulgaris, verruca planae, verruca seborroica, filiform warts, mosaic warts, etc., caused by virus, and molluscs, caused by poxvirus. The cosmetic method comprises an application of a nitric oxide (NO) eluting polymer arranged to contact the area to be treated, such that a cosmetic dose of nitric oxide is eluted from said nitric oxide eluting polymer to said area.

According to another aspect of the invention, a device is provided that allows for target treatment of cosmetic disorders, caused by chronological age, environmental factors, changes in physiological functions of skin, such as psoriasis, dermatitis, cellulites, and viral and/or bacteriological attacks, for example herpes, such as Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, warts, such as verruca vulgaris, verruca planae, verruca seborroica, filiform warts, mosaic warts, etc., caused by virus, and molluscs, caused by poxvirus. The device comprises a nitric oxide (NO) eluting polymer arranged to contact the area to be treated, such that a cosmetic dose of nitric oxide is eluted from said nitric oxide eluting polymer to said area. According to another aspect of the invention, a manufacturing process for such a cosmetic treatment device is provided, wherein the process is a process for forming a device that allows for target treatment of cosmetic disorders, caused by chronological age, environmental factors, changes in physiological functions of skin, such as psoriasis, dermatitis, cellulites, and viral and/or bacteriological attacks, for example herpes, such as Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, warts, such as verruca vulgaris, verruca planae, verruca seborroica, filiform warts, mosaic warts, etc., caused by virus, and molluscs, caused by poxvirus. The process comprises selecting a plurality of nitric oxide eluting polymeric particles, such as nano fibres, fibres, nano particles, or microspeheres, and deploying said nitric oxide eluting particles in a condom/sheath or tape/coating to be comprised in said device. Alternatively the NO eluting particles are admixed to an ointment, cream, gel or foam.

The present invention has at least the advantage over the prior art that it provides target exposure of an area to be cosmetically treated to NO, whereby blood perfusion and vasodilatation are increased, whereby the supply of nutrients increase, simultaneously as an anti-viral, and an anti-microbial, effect is achievable.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF THE INVENTION

Figure 1A:
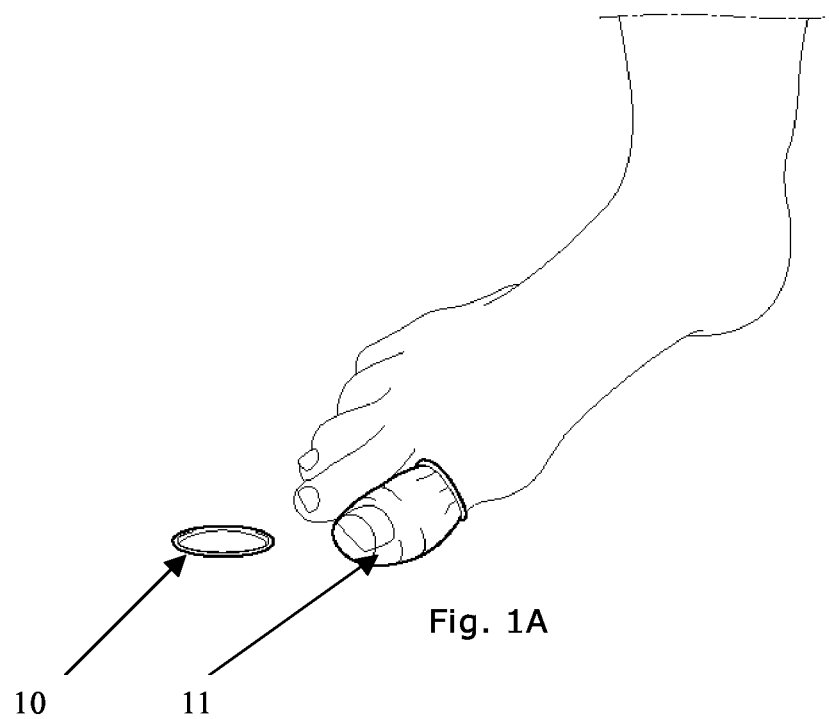
FIGS. 1A and 1B are schematic illustrations of a condom/sheath according to an embodiment of the device of the present invention.

The following description focuses on embodiments of the present invention applicable to a device, which allows for target treatment of cosmetic disorders, for instance caused by chronological age, environmental factors, changes in physiological functions of skin, acne, psoriasis, dermatitis, cellulites, viral and/or bacteriological attacks, such as herpes, for example Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, warts, such as verruca vulgaris, verruca planae, verruca seborroica, filiform warts, mosaic warts, etc., caused by virus, and molluscs, caused by poxvirus.

With regard to nitric oxide (nitrogen monoxide, NO), its physiological and pharmacological roles have attracted much attention and thus have been studied. NO is synthesized from arginine as the substrate by nitric oxide synthase (NOS). NOS is classified into a constitutive enzyme, cNOS, which is present even in the normal state of a living body and an inducible enzyme, iNOS, which is produced in a large amount in response to a certain stimulus. It is known that, as compared with the concentration of NO produced by cNOS, the concentration of NO produced by iNOS is 2 to 3 orders higher, and that iNOS produces an extremely large amount of NO.

In the case of the generation of a large amount of NO as in the case of the production by iNOS, it is known that NO reacts with active oxygen to attack exogenous microorganisms and cancer cells, but also to cause inflammation and tissue injury. On the other hand, in the case of the generation of a small amount of NO as in the case of the production by cNOS, it is considered that NO takes charge of various protective actions for a living body through cyclic GMP (cGMP), such as vasodilator action, improvement of the blood circulation, antiplatelet-aggregating action, antibacterial action, anticancer action, acceleration of the absorption at the digestive tract, renal function regulation, neurotransmitting action, erection (reproduction), learning, appetite, and the like. Heretofore, inhibitors of the enzymatic activity of NOS have been examined for the purpose of preventing inflammation and tissue injury, which are considered to be attributable to NO generated in a large amount in a living body. However, the promotion of the enzymatic activity (or expressed amount) of NOS (in particular, cNOS) has not been examined for the purpose of exhibiting various protective actions for a living body by promoting the enzymatic activity of NOS and producing NO appropriately.

In recent years research has been directed to polymers with the capability of releasing nitrogen oxide when getting in contact with water. Such polymers are for example polyalkyleneimines, such as L-PEI (Linear PolyEthylenelmine) and B-PEI (Branched PolyEthylenelmine), which polymers have the advantage of being biocompatible. Another advantage is that NO is released without any secondary products that could lead to undesired side effects. NO is released without by-products or breakdown products.

The polymers according to the present invention may be manufactured by electro spinning, air spinning, gas spinning, wet spinning, dry spinning, melt spinning, or gel spinning. Electro spinning is a process by which a suspended polymer is charged. At a characteristic voltage a fine jet of polymer releases from the surface in response to the tensile forces generated by interaction by an applied electric field with the electrical charge carried by the jet. This process produces a bundle of polymer fibres, such as nano-fibres. This jet of polymer fibres may be directed to a surface to be treated.

Furthermore, U.S. Pat. No. 6,382,526, U.S. Pat. No. 6,520,425, and U.S. Pat. No. 6,695,992 disclose processes and apparatuses for the production of such polymeric fibres. These techniques are generally based on gas stream spinning, also known within the fiber forming industry as air spinning, of liquids and/or solutions capable of forming fibers.

Other example for NO eluting polymers are given in U.S. Pat. No. 5,770,645, wherein polymers derivatized with at least one —NOX group per 1200 atomic mass unit of the polymer are disclosed, X being one or two. One example is an S-nitrosylated polymer and is prepared by reacting a polythiolated polymer with a nitrosylating agent under conditions suitable for nitrosylating free thiol groups.

Akron University has developed NO-eluting L-PEI molecule that can be nano-spun onto the surface of permanently implanted medical devices, such as implanted grafts, showing significant improvement of the healing process and reduced inflammation when implanting such devices.

According to U.S. Pat. No. 6,737,447, a coating for medical devices provides nitric oxide delivery using nanofibers of linear poly (ethylenimine)-iazeniumdiolate. Linear poly (ethylenimine) diazeniumdiolate releases nitric oxide (NO) in a controlled manner.

However, the meaning of "controlled" in the context of U.S. Pat. No. 6,737,447 is only directed to the fact that nitric oxide is eluted from the coating during a period of time, i.e. that the nitric oxide not is eluted all in once. Therefore, the interpretation of "controlled" in respect of U.S. Pat. No. 6,737,447 is different from the meaning of "regulating" in the present invention. "Regulate or control", according to the present invention is intended to be interpreted as the possibility to vary the elution of nitric oxide to thereby achieve different elution profiles.

A polymer comprising an O-nitrosylated group is also a possible nitric oxide eluting polymer. Thus, in one embodiment of the present invention, the nitric oxide eluting polymer comprises diazeniumdiolate groups, S-nitrosylated and O-nitrosylated groups, or any combinations thereof.

In still another embodiment of the present invention said nitric oxide eluting polymer is a poly (alkyleneimine) diazeniumdiolate, such as L-PEI-NO (linear poly (ethyleneimine) diazeniumdiolate), where said nitric oxide eluting polymer is loaded with nitric oxide through the diazeniumdiolate groups and arranged to release nitric oxide at a treatment site.

Some other examples of a suitable nitric oxide eluting polymer are selected from the group comprising mino cellulose, amino dextrans, chitosan, aminated chitosan, polyethyleneimine, PEI-cellulose, polypropyleneimine, polybutyleneimine, polyurethane, poly (buthanediol spermate), poly (iminocarbonate), polypeptide, Carboxy Methyl Cellulose (CMC), polystyrene, poly (vinyl chloride), and polydimethylsiloxane, or any combinations of these, and these mentioned polymers grafted to an inert backbone, such as a polysaccharide backbone or cellulosic backbone.

In still another embodiment of the present invention the nitric oxide eluting polymer may be an O-derivatized NONOate. This kind of polymer often needs an enzymatic reaction to release nitric oxide.

Other ways of describing polymers, which may be suitable as nitric oxide eluting polymer, is polymers comprising secondary amine groups (=N—H), such as L-PEI, or have a secondary amine (=N—H) as a pendant, such as aminocellulose.

In one embodiment the device is in form of fibres, nano-particles, or micro-spheres of a NO eluting polymer, which fibres, nano-particles, or micro-spheres are be integrated in a gel, cream, or foam, that may either be in a smearing or compressed structure.

In still another embodiment the nitric oxide eluting polymer, such as powder, nano-particles or micro-spheres, may be incorporated in foam. The foam may have an open cell structure, which facilitates the transport of the proton donor to the nitric oxide eluting polymer. The foam may be of any suitable polymer such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, poly (acrylic acid), Carboxy Methyl Cellulose (CMC), protein based polymers, gelatine, biodegradable polymers, cotton polyolefins, and latex, or any combinations of these.

In another embodiment the device is in form of a cream, a gel or a combination of the two. Since the nitric oxide eluting polymer is activated by proton donors the nitric oxide eluting polymer has to be separate from the proton donor until one wants to initiate the elution of nitric oxide, i.e. use the device. One way to accomplish this is to have a syringe with two separate containers. One of the containers contains a proton donor-based gel and in the other container a non proton donor-based gel, comprising the nitric oxide eluting polymer, is contained. Upon using the syringe like device, the two gels are squeezed from the syringe and mixed together, whereupon the proton donor in the first gel comes in contact with the nitric oxide eluting polymer in the second gel and the elution of nitric oxide starts. That means, two components are advantageously admixed from a self-contained unit upon administration to a cosmetic treatment site.

These fibres, nano-particles, or micro-spheres, may be formed from the NO-eluting polymers comprised in the present invention, for example polyalkyleneimines, such as L-PEI (Linear PolyEthylenelmine) and B-PEI (Branched PolyEthylenelmine), which polymers have the advantage of being biocompatible, after the release of nitrogen oxide. They may also be encapsulated in any suitable carrier material, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly (acrylic acid), Carboxy Methyl Cellulose (CMC), protein based polymers, gelatine, biodegradable polymers, cotton, and latex, or any combinations of these.

In the context of the present invention the term "encapsulating" is intended to be interpreted as fixating the nitric oxide eluting polymer in a three dimensional matrix such as a foam, a film, a nonwoven mat of nano-fibers or fibers, other materials with the capability to fixate the NO eluting polymer, or enclosing the nitric oxide eluting polymer in any suitable material.

According to an embodiment, the device is in the form of a lipstick-like device, which makes the NO especially easily applied to the skin or lips. Alternatively the gel cream, or foam is in form of or a dermatological ointment, cream or lotion for easy application to the body, e.g. in form of a spray bottle or a tube for easy application.

The device according to the present invention is applied on the area to be treated, such as any part of the body in need of improved cosmetic appearance, such as the face, neck, shoulders, hands, arms, back, chest, stomach, bottom, thigh, genitals, lower leg, and/or foot. Some places on the human body are of special interest for a majority of the population, such as the face, for the treatment of cosmetic deficiencies caused by or related to herpes, acne, wrinkles, sagging, loss of elasticity, loss of water-holding capacity, uneven distribution of fat, and the thigh, for the treatment of cellulites. Although these body parts commonly attract the most interest of the population, the present invention is not in any way intended to be limited to these.

When the gel, cream, or foam according to the present invention has been applied an elution of NO is initiated by adding a proton donor, such as water, in any possible way. This may for example be accomplished by applying a water soaked patch on said gel, gel, cream, or foam, or spraying or bathing said gel, cream, or foam with water.

The cosmetic effect is obtained, as the NO eluting polymer elutes NO on the area to be treated, by an increased blood perfusion and vasodilatation, whereby an increased supply of nutrients in the tissue of interest is achieved. The increased blood perfusion and vasodilatation may, in another embodiment of the present invention, result in an improved effect when combined with other skin care products. Thus, this synergistic effect is within the scope of the present invention.

The fibres, nano-particles, or micro-spheres may also be integrated in a hydrogel, which is mixed directly before use.

This embodiment has the advantage of being able to penetrate pockets and corners in the skin for closer elution of NO on the area to be treated.

Figure 1B:
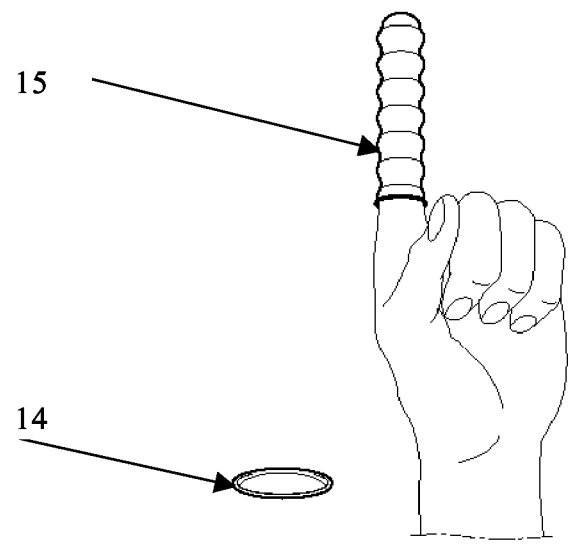

In another embodiment, according to FIGS. 1A and 1B, the device according to the present invention is in form of a latex or rubber condom/sheath, said condom/sheath being covered with nano-filament of any of the NO-eluting polymers according to above, such as polyalkyleneimines, such as L-PEI (Linear PolyEthylenelmine) and B-PEI (Branched PolyEthylenelmine), which polymers have the advantage of being biocompatible, after the release of nitrogen oxide. FIG. 1A shows such a condom/sheath in a rolled-up form 10, and put onto an exemplary toe in a rolled-on form 11. FIG. 1B shows such a condom/sheath in a rolled-up form 14, and put onto an exemplary finger in a rolled-on form 15. A during condom has for instance the advantage that it during storage and transportation offers a protection against an undesired release of NO prior to intended use, as the rolled-up form 10,14 of the condom/sheath safely encloses the NO-releasing material, even if a NO releasing factor, for instance humidity, eventually should enter a package in which the condom/sheath is packed prior to use.

In another embodiment the condom/sheath is covered on the inside with nano-filament of L-PEI.

This condom/sheath may be in any suitable size, such as a suitable size for rolling said condom/sheath over the thigh, arm, neck, head, foot etc., to be treated. These sizes may for example vary from small, medium, and large sized condoms/sheaths in accordance with the different sizes, in respect of the different body parts, of persons in the population. The condom/sheath may even have a size suitable for covering a foot, such as a sock 24, or a foot-condom/sheath, as shown in FIG. 2C, or other specific part of the body, to be able to obtain a cosmetic treatment. According to an embodiment, the condoms/sheaths are coated with NO eluting nano fibres. According to another embodiment the condoms/sheaths are made of, or comprise nanofilaments, e.g. made by electro or gas jet spinning. According to a further embodiment the condoms/sheaths comprises microspheres eluting NO in use. Preferably the three aforementioned embodiments employ L-PEI material loaded with NO. Activation on NO release may be done by e.g. foot sweat, water sprayed onto the condoms/sheaths immediately prior to use, or a water bag configured for releasing water upon activation, e.g. by pushing onto the bag thus bursting (see below).

When the NO-eluting condom/sheath according to certain embodiments is treated with or gets in contact with the moisture, in form of secreted sweat, the NO-eluting condom/sheath starts to release NO to the area to be treated. Alternatively the device is moistured or wettened, with a proton donor, immediately prior to application or use for controlling or activating the NO release.

In another embodiment the condom/sheath is covered on the inside with NO-eluting nano-particles, or microspheres, according to above.

When the nano-particles, or micro-spheres, according to this embodiment, gets in contact with the secreted moisture, in form of sweat, on the inside of the condom/sheath, they start to elute NO on the area to be treated.

In yet another embodiment the condom/sheath contains a small proton donor bag or sealed proton donor sponge. This proton donor bag or sealed proton donor sponge is used to activate the elution of NO from the NO-eluting nanoparticles, or micro-spheres. This proton donor bag or sealed proton donor sponge may be located in the tip of the condom/sheath according to the invention. Persons that not easily sweat may be helped by the use of this embodiment.

In another embodiment of the present invention a nitric oxide eluting polymer is provided, and/or combined, with microencapsulated proton donor.

This may for example be done by first manufacture micro capsules, containing a proton donor, such as water or water containing liquid, in a state of the art manner. These micro capsules are then applied on the NO eluting polymer. The application of the micro capsules on the NO eluting polymer may for example be done by gluing, such as pattern gluing, or instead spinning the NO eluting polymer onto said micro capsules. In this way a device or a system, comprising NO eluting polymer and micro encapsulated proton donor is manufactured. When the device or system is applied on the target area the device or system is compressed or squeezed. Said compression or squeezing results in breakage of the micro capsules. The NO eluting polymer is thus exposed to proton donor, and the elution of NO from the NO eluting polymer is initiated on the target area. In other embodiments of the present invention the proton donor inside the micro capsules is released by heating or shearing the micro capsules until the micro capsules are ruptured.

In still another embodiment the micro capsules are formed into a film, tape, or sheath. Thereafter, a film, tape, or sheath of an NO eluting polymer is glued onto the film, tape, or sheath of micro capsules. Preferably the film, tape, or sheath of the NO eluting polymer is glued onto the film, tape, or sheath of the micro capsules in patterned way. The obtained pattern includes spaces where there is no glue, in which spaces the proton donor will be transported to the NO eluting polymer once the micro capsules are broken from compression or squeezing. When the proton donor gets in contact with the NO eluting polymer the elution of NO starts. Thus, the combination of film, tape, or sheath of micro capsules and NO eluting polymer may be applied on a target area. Thereafter the combination is compressed or squeezed, which results in that the target area is exposed to NO.

In yet another embodiment the NO eluting polymer is spun directly onto the film, tape, or sheath of micro capsules, containing proton donor. The combination of film, tape, or sheath of micro capsules and spun NO eluting polymer may be applied on a target area. Thereafter the combination is compressed or squeezed, which results in that the target area is exposed to NO.

In still another embodiment of the present invention the device or system is provided with an activation indicator. This activation indicator indicates when the micro capsules are satisfyingly broken, hence when the NO eluting polymer is subjected to enough proton donor to elute an efficient amount of NO. This activation indicator may for example be obtained by colouring the proton donor that is trapped inside the micro capsules. When the micro capsules are broken the coloured proton donor escapes the microcapsules and the colour gets visualised while efficiently wetting the NO eluting polymer. Another way of obtaining an activation indicator is to choose to manufacture the micro capsules in a material, or choose a wall thickness of said micro particles, that creates a sound when the micro capsules break. It is also possible to admix a scent in the proton donor, contained in the micro capsules. This results in that the user of the device or system may smell the scent when the proton donor escapes from the micro capsules after breakage thereof.

In another embodiment a substance that changes color when it comes in contact with water may be incorporated in embodiments of the inventive device. Thus when the water capsules or water bag breaks the material changes color, thereby indicating that the material is activated. This may also comprise the subsequent activation of different areas of a cosmetic treatment device in order to prolong the usable period of such a device.

In another embodiment of the present invention the device or system only allows directed target NO-elution in one direction. In this kind of embodiment one side of the device according to the invention has low permeability, or substantially no permeability, to nitric oxide. This may be accomplished by applying a material on one side of the device according to the invention that is not permeable to NO. Such materials may be chosen from the group comprising common plastics, such as fluoropolymers, polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly (acrylic acid), Carboxy Methyl Cellulose (CMC), protein based polymers, gelatine, biodegradable polymers, cotton, and latex, or any combinations of these. This embodiment is also easy to manufacture as the NO eluting polymer, e.g. L-PEI (or nitric oxide eluting polymer and carrier material, which will be explained in more detail below) may be electro or gas-jet spun onto the surface of the device according to the invention of e.g. the mentioned plastics, latex, or cotton.

In still another embodiment the device is provided with one membrane, which is permeable to nitric oxide, on a first side of the device, and another membrane, which has low permeability or substantially no permeability to nitric oxide, on a second side of said device. This embodiment provides the possibility to direct the elution to said first side of the device, while the elution of nitric oxide is substantially prevented from said second side. Thereby, a greater amount of nitric oxide will reach the intended area to be treated, rendering the device more effective.

The activation of the nitric oxide eluting polymer may be accomplished by contacting said polymer with a suitable proton donor. In one embodiment the proton donor may be selected from the group comprising water, body fluids (blood, lymph, bile, etc.), alcohols (methanol, ethanol, propanols, buthanols, pentanols, hexanols, phenols, naphtols, polyols, etc.), aqueous acidic buffers (phosphates, succinates, carbonates, acetates, formats, propionates, butyrates, fatty acids, amino acids, etc.), or any combinations of these.

By adding a surfactant in the proton donor one can facilitate the wettening of the device. The surfactant lowers the surface tension and the activating fluid is easily transported throughout the device.

Figure 2A:
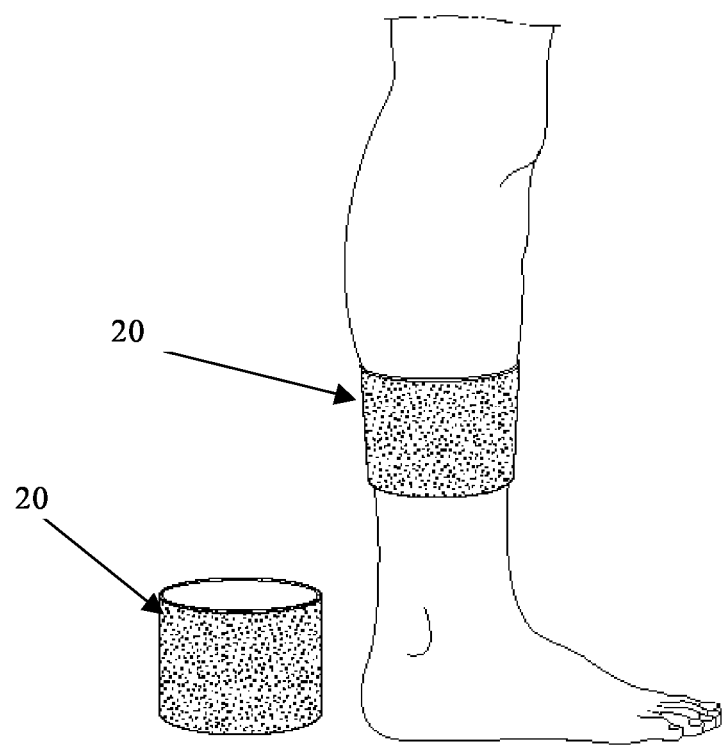
FIGS. 2A and 2B, are schematic illustrations of a tape or coating according to an embodiment of the device of the present invention.
Figure 2B:
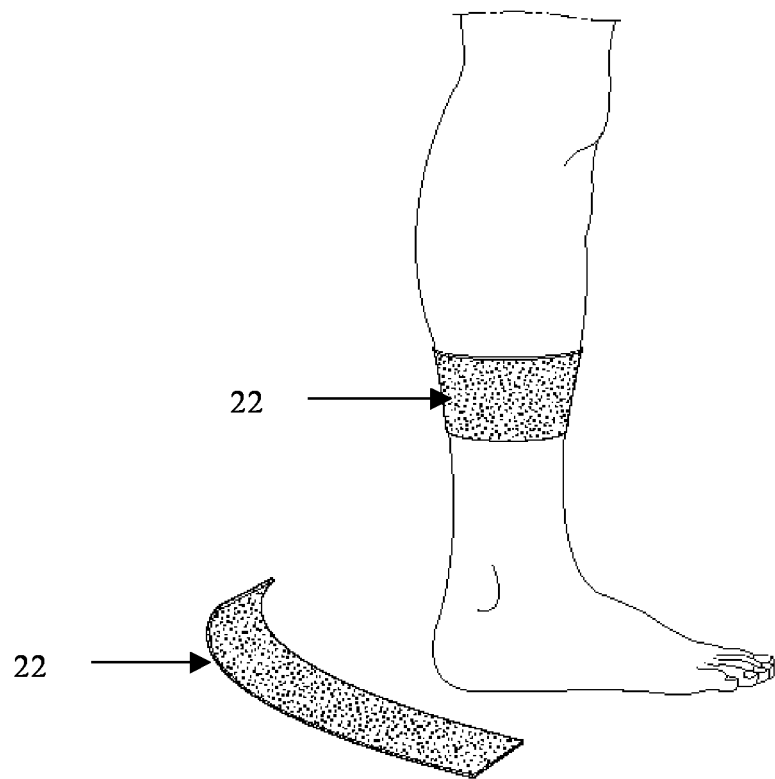
Figure 2C:
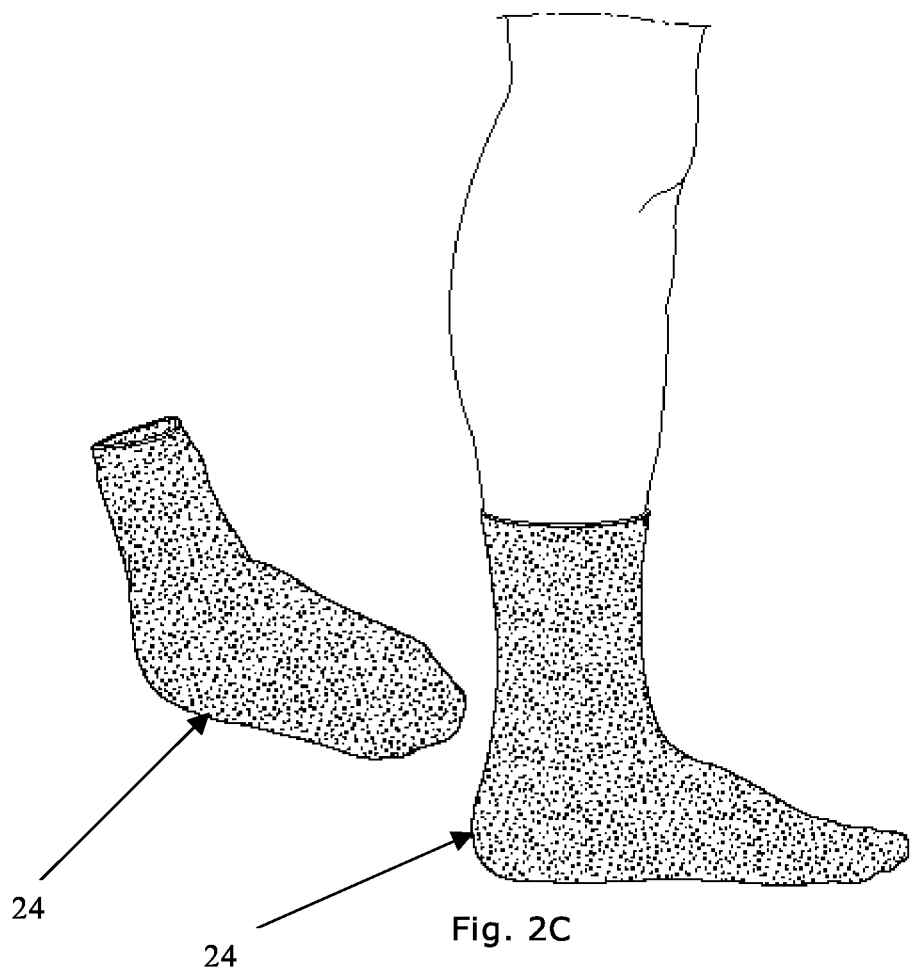
FIG. 2C is a schematic illustration of a sock according to an embodiment of the device of the present invention.

In still another embodiment of the device, said device may be manufactured in the form of a polyurethane, or polyethylene, tape 22 or coating 20, according to FIG. 2A or 2B. This polyurethane tape or coating may easily be wrapped around, or applied on, the area to be cosmetically treated. At least the side facing the body part, may be covered with NO-eluting nano-particles, or micro-spheres, or nano-filament of NO-eluting L-PEI. When these particles or filaments get in contact with the moisture, in form of sweat, on the inside of the tape or coating, the elution of NO starts. When the tape/coating on the exterior is has a gas tight layer, directed target treatment with released NO is implementable.

For certain embodiments, a gas permeable layer may be provided for towards the cosmetic treatment area. This gas permeable layer may further be liquid impermeable, such as made of Gore-Tex® or a similar material. In this manner the target area is kept dry from an eventually used NO releasing activation liquid, offering more comfort to the user of the cosmetic device.

Figure 3:
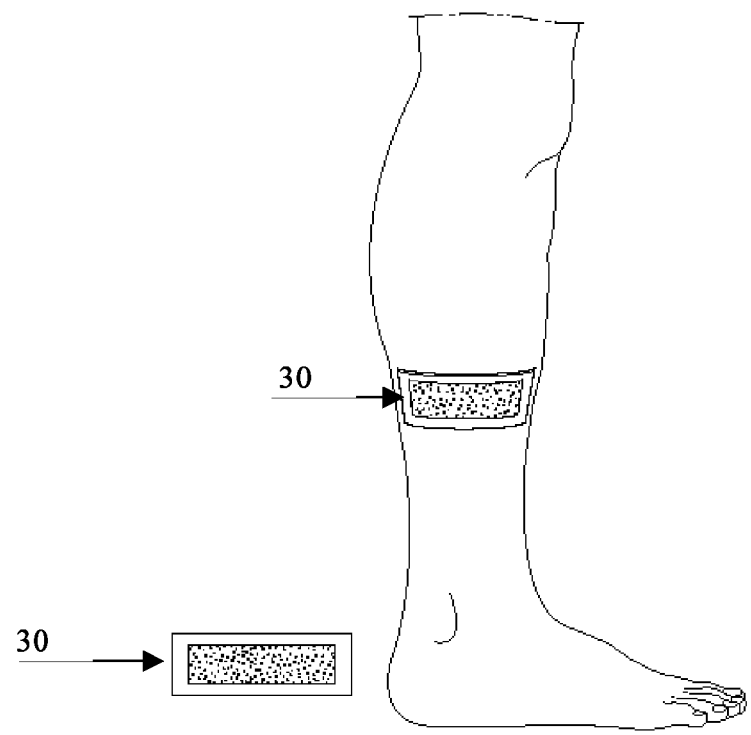
FIG. 3 is a schematic illustration of a patch/pad according to an embodiment of the device of the present invention.

In another embodiment of the device according to the present invention, said device is in form of a patch/pad 30, according to FIG. 3, which patch/pad is suitable to be applied on the face, arm, hand, thigh, back, stomach, neck, to be cosmetically treated, or onto other areas that are difficult to cover with the condom/sheath according to the present invention. This patch/pad 30 is attached by any-suitable adhering means, such as materials that adhere to the skin.

Of course, in other embodiments of the invention, the patch/pad or tape/coating may be manufactured by any other suitable material, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly (acrylic acid), Carboxy Methyl Cellulose (CMC), protein based polymers, gelatine, biodegradable polymers, cotton, and latex, or any combinations of these. The NO-eluting polymer may be integrated in, spun together with, or spun on top of, any of these materials in all of the embodiments of the present invention.

In another embodiment these nano-particles, or micro-spheres, may be integrated in a soluble film that disintegrates on the inside of the condom/sheath or tape/coating according to the present invention, in order to elute NO at the area of interest when the soluble film gets in contact with the moisture, in form of sweat or from the water bag or sealed water sponge, on the area to be treated.

When placed on an area to be treated the device according to the present invention provides prevention and treatment of cosmetic disorders, caused by of chronological age, environmental factors, changes in physiological functions of skin, psoriasis, dermatitis, cellulites, viral and/or bacteriological attacks, for example herpes, such as Herpes Simplex Virus type 1 (HSV-1), Herpes Simplex Virus type 2 (HSV-2), Epstein Barr Virus (EBV), CytoMegaloVirus (CMV), Varicella Zoster Virus (VZV), human herpes virus 6 (exanthum subitum and roseola infantum), human herpes virus 8 (HHV-8), caposis sarcoma, probably caused by HHV-8, warts, such as verruca vulgaris, verruca planae, verruca seborroica, filiform warts, mosaic warts, etc., caused by virus, and molluscs, caused by poxvirus.

In another embodiment of the present invention the device only allows NO-elution in one direction. In this kind of embodiment one side of the condom/sheath or tape/coating is non-permeable to NO. This may be accomplished by applying a material on one side of the condom/sheath or tape/coating that is not permeable to NO. Such materials may be chosen from the group comprising common plastics, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly (acrylic acid), Carboxy Methyl Cellulose (CMC), protein based polymers, gelatine, biodegradable polymers, cotton, and latex, or any combinations of these. This embodiment is also easy to manufacture as the NO eluting polymer, e.g. L-PEI nano fibres may be electro or gas-jet spun onto the surface of a condom sheath of e.g. the mentioned plastics, latex, or cotton. In the case of a condom it may be rolled up, or a sheath may be turned outside in after manufacturing to protect the NO eluting polymer during packaging, transport and prior to use from external influences, being e.g. mechanical (abrasion of the polymer), chemical (moisture deactivating the device prior to use) etc.

In yet another embodiment the NO-eluting device is acting as a booster for drug eluting patches, i.e. the device comprises additional agents e.g. pharmaceuticals, vitamins, nicotin, nitroglycerin, diclofenac etc. This embodiment presents a device with the advantage of combining two treatments, of significant value, in one treatment.

Hence, a synergetic effect may be achieved by such devices when NO that is eluted from the device. NO has a vasodilatory effect on the region where the device having the combination compound actuates. Vasodilated tissue is more susceptible to certain medications and thus more easily treated by the medical preparations and still NO has in addition to that the anti-inflammatory, anti-bacterial etc. effect. Hence, an unexpected surprisingly effective treatment is provided.

The cosmetic treatment with NO eluted from a polymer may also be combined with other agents in order to enhance the cosmetic treatment, for instance a desquamating agent, a moisturizer, a depigmenting or propigmenting agent, an anti-glycation agent, a 5.alpha.-reductase inhibitor, a lysyl and/or prolyl hydroxylase inhibitor, an agent for stimulating the synthesis of dermal or epidermal macromolecules and/or for preventing their degradation, an agent for stimulating keratinocyte proliferation and/or differentiation, a muscle relaxant, a further antimicrobial agent, a tensioning agent, an anti-pollution agent or a free-radical scavenger, or a combination thereof.

Preferably the NO eluting polymer is prepared and provided in a suitable form for topical application to keratin materials, including e.g. the skin, the eyelashes and the nails. The cosmetic use of a NO eluting polymer composition is for instance used for improving the appearance of such keratin materials. The cosmetic therapy includes a variety of fields, such as a use for preventing or treating wrinkles and fine lines and/or the loss of firmness, tonicity and/or elasticity of the skin and/or a dull complexion and/or dilation of the pores and/or skin or hair pigmentation disorders and/or skin dryness and/or hyperseborrhea and/or sensitive skin, and/or eventually hair loss and/or baldness. The composition or preparation comprising the NO eluting polymer should be provided in a biocompatible and/or a physiologically acceptable medium, suitable for the topical application to the keratine material mentioned above. Suitable forms include also moisturizing creams, anti-ageing creams, skin-peeling preparations. An alternative field of application is for cosmetically fading out pigmentary marks, in particular age marks. Moreover, cosmetic skin defects caused by acne may be cosmetically treated by topical treatment with a device according to certain embodiments of the invention. Microbial colonization and inflammation may be removed in order to improve the appearance of acne exposed skin, for instance by the anti-inflammatory potency and/or the antibacterial potency without inducing bacterial resistance of NO.

One of the most common infections in the world is caused by Human Papilloma Virus (HPV), commonly known as the warts virus. It is a microscopic virus particle that infects the skin, causing warts or genital warts. The warts/genital warts appear as single bumps or in clusters some having a cauliflower structure. There are many strains or types of the HPV (warts) virus. The warts virus is also found in the genital area in men and woman (Genital Warts) including in and around the anus, vagina, and penis, otherwise known as anal warts, vaginal warts and penis warts.

Genital Warts and HPV are a serious health concern. For woman, genital warts (vaginal) have been linked to cervical as well as other types of genital cancers. Male genital warts and female genital warts can also lead to cancer. Male genital warts are extremely common, and genital warts are as common in woman too. It is therefore extremely important to treat genital warts as soon as you are aware of their presence. Any sexual or skin to skin contact with other people should be avoided the genital warts are removed, otherwise there is a substantial risk of passing the HPV virus on, and possibly infecting others with genital warts too. The device herein described may therapeutically treat such warts advantageously. However, the present application is directed to the cosmetic side effects of such warts, e.g. scars formed during or after the removal of the warts. The device of some embodiments of the invention may be applied topically onto the genital warts or regular warts using e.g. a cotton stick.

Certain embodiments may provide for cosmetic scar reduction.

Erectile dysfunction, or ED, can be a total inability to achieve erection, an inconsistent ability to do so, or a tendency to sustain only brief erections. These variations make defining ED and estimating its incidence difficult. Estimates range from 15 million to 30 million, depending on the definition used. According to the National Ambulatory Medical Care Survey (NAMCS), for every 1,000 men in the United States, 7.7 physician office visits were made for ED in 1985. By 1999, that rate had nearly tripled to 22.3. The increase happened gradually, presumably as treatments such as vacuum devices and injectable drugs became more widely available and discussing erectile function became accepted. Perhaps the most publicized advance was the introduction of the oral drug sildenafil citrate (Viagra) in March 1998. NAMCS data on new drugs show an estimated 2.6 million mentions of Viagra at physician office visits in 1999, and one-third of those mentions occurred during visits for a diagnosis other than ED.

In older men, ED usually has a physical cause, such as disease, injury, or side effects of drugs. Any disorder that causes injury to the nerves or impairs blood flow in the penis has the potential to cause ED. Incidence increases with age: About 5 percent of 40-year-old men and between 15 and 25 percent of 65-year-old men experience ED.

The internal structure of the penis consists of two cylinder-shaped vascular tissue bodies (corpora cavernosa) that run throughout the penis; the urethra (tube for expelling urine and ejaculate); erectile tissue surrounding the urethra; two main arteries; and several veins and nerves. The longest part of the penis is the shaft, at the end of which is the head, or glans penis. The opening at the tip of the glans, which allows for urination and ejaculation, is the meatus. The physiological process of erection begins in the brain and involves the nervous and vascular systems. Neurotransmitters in the brain (e.g., epinephrine, acetylcholine, nitric oxide) are some of the chemicals that initiate it. Physical or psychological stimulation (arousal) causes nerves to send messages to the vascular system, which results in significant blood flow to the penis. Two arteries in the penis supply blood to erectile tissue and the corpora cavernosa, which become engorged and expand as a result of increased blood flow and pressure. Because blood must stay in the penis to maintain rigidity, erectile tissue is enclosed by fibrous elastic sheathes (tunicae) that cinch to prevent blood from leaving the penis during erection. When stimulation ends, or following ejaculation, pressure in the penis decreases, blood is released, and the penis resumes its normal shape.

A usual method of treatment for ED is that oral medications are used to treat erectile dysfunction include selective enzyme inhibitors, e.g., sildenafil (Viagra™], vardenafil HCl (Levitra™), tadalafil (Clalis™) and yohimbine (Yohimbine™). Selective enzyme inhibitors are may be taken up to once a day to treat ED. They improve partial erections by inhibiting the enzyme that facilitates their reduction and increase levels of cyclic guanosine monophosphate (cGMP, a chemical factor in metabolism), which causes the smooth muscles of the penis to relax, enabling blood to flow into the corpora cavernosa. However, patients taking nitrate drugs (used to treat chest pain) and those taking alpha-blockers (used to treat high blood pressure and benign prostatic hyperplasia) should not take selective enzyme inhibitors. Men who have had a heart attack or stroke within the past 6 months and those with certain medical conditions (e.g., uncontrolled high blood pressure, severe low blood pressure or liver disease, unstable angina) that make sexual activity inadvisable should not take Clalis™. Dosages of the drug should be limited in patients with kidney or liver disorders. Viagra™ is absorbed and processed rapidly by the body and is usually taken 30 minutes to 1 hour before intercourse. Results vary depending on the cause of erectile dysfunction, and studies have shown that Viagra is not always effective, e.g. it helps men with erectile dysfunction associated with diabetes mellitus in 57% and radical prostatectomy in 43% within 30 minutes and enhances the ability to achieve erection for up to 36 hours. Common side effects of selective enzyme inhibitors include headache, reddening of the face and neck (flushing), indigestion, and nasal congestion. Cialis™ may cause muscle aches and back pain. Yohimbine improves erections for a small percentage of men. It stimulates the parasympathetic nervous system, which is linked to erection, and may increase libido. It is necessary to take the medication for 6 to 8 weeks before determining whether it will work or not. Yohimbine has a stimulatory effect and side effects include elevated heart rate and blood pressure, mild dizziness, nervousness, and irritability. Yohimbine's effects have not been studied thoroughly, but some studies suggest that 10% to 20% of men respond to treatment with the drug.

Self-injection involves using a short needle to inject medication through the side of the penis directly into the corpus cavernosum, which produces an erection that lasts from 30 minutes to several hours. Side effects of such self-injections include infection, bleeding, and bruising at the injection site, dizziness, heart palpitations, and flushing. There is a small risk for priapism, i.e. an erection that lasts for more than 6 hours and requires medical relief. Repeated injection may cause scarring of erectile tissue, which can further impair erection.

The device herein described may therapeutically treat erectile dysfunction, without the above-mentioned side-effects. For instance the herein described condom is well suited for this purpose, as well as other embodiments, e.g. gels or creams. However, the present application is directed to the treatment of possible cosmetic side effects of conventional ED treatments, e.g. the above-mentioned scars resulting from self-injections.

The cosmetic treatment device elutes according to certain embodiments nitric oxide (NO) from an eluting polymer in a therapeutic dose, such as between 0.001 to 5000 ppm, such as 0.01 to 3000 ppm, such as 0.1 to 1000 ppm, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 91, 92, 93, 94, 95, 96, 97, 98, 99, or 100 ppm. The concentration may vary widely depending on where the concentration is measured. If the concentration is measured close to the actual NO eluting polymer the concentration may be as high as thousands of ppm, while the concentration inside the tissue in this case often is considerably lower, such as between 1 to 1000 ppm.

Three important factors in controlling and regulating the elution of nitric oxide from a nitric oxide eluting polymer are how quickly a proton donor comes in contact with the nitric oxide releasing polymer, such as a diazoliumdiolate group, the acidity of the environment surrounding the nitric oxide eluting polymer, and the temperature of the environment surrounding the nitric oxide releasing polymer (higher temperature promotes elution of nitric oxide).

In the embodiments of the present invention it may be suitable to control or regulate the time span of NO release from the device according to the invention. This may be accomplished by integrating other polymers or materials in said device. These polymers or materials may be chosen from any suitable material or polymer, such as polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly (acrylic acid), Carboxy Methyl Cellulose (CMC), protein based polymers, gelatine, biodegradable polymers, cotton, and latex, or any combinations of these.

Figure 4:
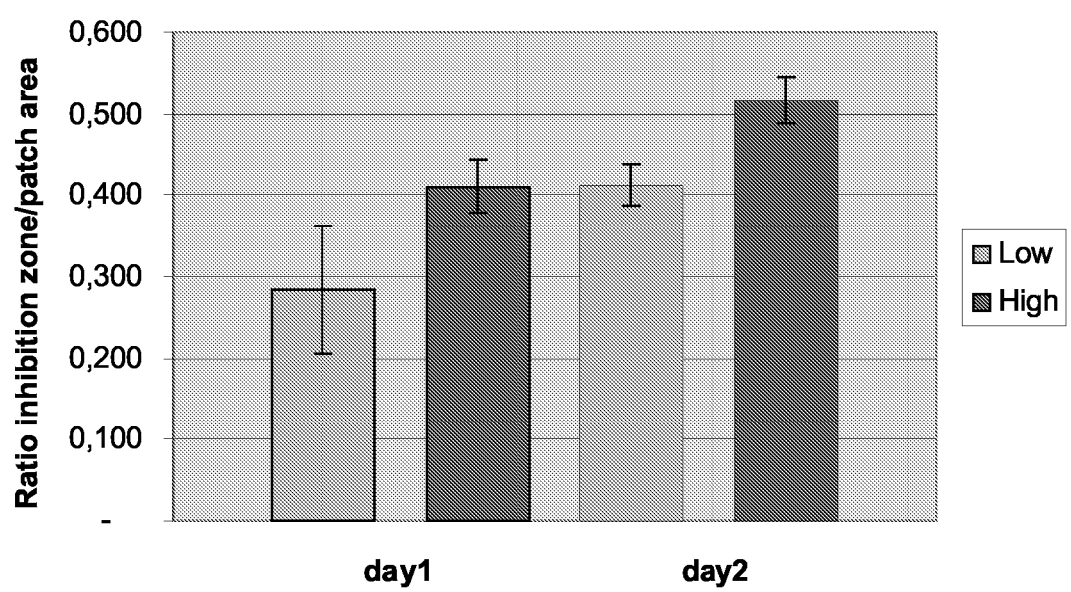
FIG. 4 is chart showing an illustration of two different elution profiles for two different mixtures of nitric oxide eluting polymer and carrier material.

In one embodiment of the present invention a nitric oxide eluting polymer, such as L-PEI-NO, is mixed with a carrier polymer to slow down or prolong the elution of nitric oxide. Also, in another embodiment, the nitric oxide eluting polymer may be mixed with more than one carrier polymer, whereby be elution or release may be tailor made to fit specific needs. Such a need may for example be a low elution during a first period of time, when the environment of the nitric oxide eluting polymer is hydrophobic, and a faster elution during a second period of time, when the environment of the nitric oxide eluting polymer has been altered to be more hydrophilic. This may for example be accomplished by using biodegradable polymers, whereby a low elution during a first period of time is obtained, after which, when the hydrophobic polymer has been dissolved, the hydrophilic polymer provides a higher elution of nitric oxide. Thus, a more hydrophobic carrier polymer will give a slower elution of nitric oxide, since the activating proton donor, such as water or body fluid, will penetrate the carrier polymer slower. On the other hand, a hydrophilic polymer acts the opposite way. One example of an hydrophilic polymer is polyethylene oxide, and one example of an hydrophobic polymer is polystyrene. These carrier polymers may be mixed with the nitric oxide eluting polymer and then electrospun to suitable fibers. The skilled person in the art knows which other polymers may be used for similar purposes. FIG. 4 illustrates two elution profiles (NO concentration vs. time) for two different polymer mixtures; a nitric oxide eluting polymer mixed with a hydrophilic carrier polymer in an acidic environment (A), and a nitric oxide eluting polymer mixed with a hydrophobic carrier polymer in a neutral environment (B). In one embodiment this carrier polymer is substituted by another material with hydrophobic or hydrophilic properties. Therefore, the term "carrier material" in the present context should be interpreted to include carrier polymers and other materials with hydrophilic or hydrophobic properties. Some embodiments may also comprise using different hydrogels in order to suitably incorporate different release characteristics.

In another embodiment of the present invention the elution of nitric oxide from a nitric oxide eluting polymer, such as L-PEI-NO, is influenced by the presence of protons. This means that a more acidic environment provides a quicker elution of nitric oxide. By activating the nitric oxide eluting polymer, or mixture of nitric oxide eluting polymer and carrier material, with an acidic fluid, such as an ascorbic acid solution, the elution of nitric oxide may be accelerated.

The carrier polymers and carrier materials mentioned above may in addition affect other characteristics than the regulation of nitric oxide elution. An example of such a characteristic is mechanical strength. Hence, advantageous devices may be produced according to specific application requirements.

In respect of the carrier polymers or carrier materials, the NO-eluting polymer may be integrated in, spun together with, or spun on top of, any of these materials in all of the embodiments of the present invention. This spinning includes electro spinning, air spinning, dry spinning, wet spinning, melt spinning, and gel spinning. In this way, one may manufacture fibers of a polymer mixture, comprising a nitric oxide eluting polymer and a carrier polymer, or a carrier material, with predefined nitric oxide eluting characteristics. These characteristics may be tailor made for different elution profiles in different applications.

The NO-eluting polymers in the devices according to the present invention may be combined with silver, such as hydroactivated silver. The integration of silver in the devices according to the present invention gives the healing process an extra boost. Preferably the silver is releasable from the devices in the form of silver ions. The integration of silver in the device may present several advantages. One example of such an advantage is that the silver may keep the device in itself free from bacteria or viruses, while the nitric oxide eluting polymer elutes the therapeutic dosage of nitric oxide to the target site.

The nitric oxide eluting polymer may comprise a secondary amine, either in the backbone or as a pendant, as described previously. This will make a good nitric oxide eluting polymer. The secondary amine should have a strong negative charge to be easy to load with nitric oxide. If there is a ligand close to the secondary amine, such as on a neighbour atom, such as a carbon atom, to the nitrogen atom, with higher electronegativity than nitrogen (N), it is very difficult to load the polymer with nitric oxide. On the other hand, if there is a electropositive ligand close to the secondary amine, such as on a neighbour atom, such as a carbon atom, to the nitrogen atom, the electronegativity of the amine will increase and thereby increase the possibility to load the nitric oxide elution polymer with nitric oxide.

In an embodiment of the present invention the nitric oxide polymer may be stabilized with a salt. Since the nitric oxide eluting group, such as a diazeniumdiolate group, usually is negative, a positive counter ion, such as a cation, may be used to stabilize the nitric oxide eluting group. This cation may for example be selected from the group comprising any cation from group 1 or group 2 in the periodic table, such as $Na+$, $K+$, $Li+$, $Be2+$, $Ca2+$, $Mg2+$, $Ba2+$, and/or $Sr2+$. Different salts of the same nitric oxide eluting polymer have different properties. In this way a suitable salt (or cation) may be selected for different purposes. Examples of cationic stabilized polymers are L-PEI-NO-Na, i.e. L-PEI diazeniumdiolate stabilized with sodium, and L-PEI-NO-Ca, i.e. L-PEI diazeniumdiolate stabilized with calcium.

Another embodiment of the present invention comprises mixing the nitric oxide eluting polymer, or a mixture of the nitric oxide eluting polymer and a carrier material, with an absorbent agent. This embodiment provides the advantage of an accelerated elution of nitric oxide since the polymer, or polymer mixture, via the absorbent agent, may take up the activating fluid, such as water or body fluid, much faster. In one example 80% (w/w) absorbent agent is mixed with the nitric oxide eluting polymer, or mixture of nitric oxide eluting polymer and carrier material, and in another embodiment 10 to 50% (w/w) absorbent agent is mixed with the nitric oxide eluting polymer, or mixture of nitric oxide eluting polymer and carrier material.

Since the elution of nitric oxide is activated by a proton donor, such as water, it may be an advantage to keep the nitric oxide eluting polymer, or mixture of nitric oxide eluting polymer and carrier material, in contact with said proton donor. If an indication requires an elution of nitric oxide during a prolonged period of time, a system is advantageous, which presents the possibility to keep the proton donor in contact with the nitric oxide eluting polymer, or mixture of nitric oxide eluting polymer and carrier material. Therefore, in still another embodiment of the present invention, the elution of nitric oxide may be regulated by adding an absorbent agent. The absorbent agent absorbs the proton donor, such as water, and keeps the proton donor in close contact with the nitric oxide eluting polymer during prolonged periods of time. Said absorbent agent may be selected from the group comprising polyacrylates, polyethylene oxide, carboxymethylcellulose, and microcrystalline cellulose, cotton, and starch. This absorbent agent may also be used as a filling agent. In this case said filling agent may give the nitric oxide eluting polymer, or mixture of said nitric oxide eluting polymer and a carrier material, a desired texture.

The device according to the present invention may be manufactured by, for example electro spinning of L-PEI or other polymers comprising L-PEI or being arranged in combination with L-PEI. L-PEI is the charged at a characteristic voltage, and a fine jet of L-PEI releases as a bundle of L-PEI polymer fibres. This jet of polymer fibres may be directed to a surface to be treated. The surface to be treated may for example be any suitable material in respect of a device according to the present invention. The electro spun fibres of L-PEI then attach on said material and form a coating/layer of L-PEI on the device according to the invention.

It is of course possible to electro spin the other NO-eluting polymers, according to above, on the device according to the invention while still being inside the scope of the present invention.

In one embodiment the NO-eluting polymers according to the present invention are electro spun in such way that pure NO-eluting polymer fibres may be obtained.

It is also within the scope of the present invention to electro spin a NO-eluting polymer together with other suitable polymer/polymers.

Gas stream spinning, air spinning, wet spinning, dry spinning, melt spinning, or gel spinning, of said NO-eluting polymers, or combination of nitric oxide eluting polymer and carrier material, is also within the scope of the present invention and has the advantage that application of the spinned particles is not dependent on an electric charge to be applied. Hence, gas jet or air spinning is advantageous in certain fields of application, e.g. when inflammable solvents are present.

The manufacturing process according to the present invention presents the advantages of large contact surface of the NO-eluting polymer fibres with the area to be treated, effective use of NO-eluting polymer, and a cost effective way of producing the device according to the present invention.

The invention may be implemented in any suitable form. The elements and components of the embodiments according to the invention may be physically, functionally, and logically implemented in any suitable way or desired arbitrary combination. Indeed, the functionality may be implemented in a single unit, in a plurality of units, or as part of other functional units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A cosmetic treatment device configured for delivering nitric oxide (NO) to a treatment site of a body, wherein said device comprises:
   a NO eluting polymer, a carrier material, and a container containing a proton donor;
   wherein the NO eluting polymer and proton donor are separated by the container such that, upon the release of proton donor from the container, the NO eluting polymer and proton donor come into contact and thereby the elution of NO from the NO eluting polymer is activated and NO is delivered to the treatment site wherein the container containing a proton donor is a container selected from the group consisting of: a bag, a sponge, and a micro capsule.

2. The device according to claim 1, wherein the device is configured such that said elution of NO from said device in use is directed towards said treatment site.

3. The device according to claim 2, wherein said device comprises:
   a first membrane permeable to nitric oxide on a first side of the device and
   a second membrane, said second membrane having a lower permeability to nitric oxide than said first membrane on a second side of said device, wherein in use after activation of NO release from the NO eluting polymer, the first side of said device is oriented towards the treatment site and the second side of the device is oriented away from the treatment site.

4. The device according to claim 1, wherein said NO eluting polymer comprises one or more functional groups selected from the group consisting of diazeniumdiolate groups, S-nitrosylated groups, and O-nitrosylated groups.

5. The device according to claim 4, wherein said NO eluting polymer is linear poly (ethylenimine) diazeniumdiolate loaded with NO to form said diazeniumdiolate functional groups.

6. The device according to claim 1, wherein said nitric oxide eluting polymer is selected from the group consisting of amino cellulose, amino dextrans, chitosan, aminated chitosan, polyethyleneimine, PEI-cellulose, polypropyleneimane, polybutyleneimine, polyurethane, poly(butanediol spermate), poly(iminocarbonate), polypeptide, Carboxy Methyl Cellulose (CMC), polystyrene, poly(vinyl chloride), polydimethylsiloxane, and any combinations of these.

7. The device according to claim 1, wherein said device has a form selected from the group consisting of a condom, a sheath, a sock, a patch, a pad, a tape, and a coating.

8. The device according to claim 7, wherein said form comprises a form material selected from the group consisting of polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly(acrylic acid), CMC, protein based polymers, gelatin, biodegradable polymers, cotton, and latex, or and any combinations of these.

9. The device according to claim 1, wherein said proton donor is selected from the group consisting of water, methanol, ethanol, propanols, butanols, pentanols, hexanols, phenols, naphthols, polyols, phosphates, succinates, carbonates, acetates, formates, propionates, butyrates, fatty acids, and amino acids, and any combinations of these.

10. The device according to claim 1, wherein said device is partly disintegrable when subjected to said proton donor.

11. The device according to claim 1, wherein said NO eluting polymer comprises silver.

12. The device according to claim 1, wherein said NO eluting polymer is in a form selected from the group consisting of fibers, nano-particles and micro-spheres.

13. The device according to claim 12, wherein said form is provided as a substance selected from the group consisting of gel, cream, foam, and hydrogel, and combinations thereof.

14. The device according to claim 12, wherein said nano-particles or microspheres are integrated with a material selected from the group consisting of polyethylene, polypropylene, polyacrylonitxile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly(acrylic acid), CMC, protein based polymers, gelatine, biodegradable polymers, cotton, latex, and any combinations of these.

15. The device according to claim 1, wherein said carrier material is selected from the group consisting of polyethylene, polypropylene, polyacrylonitrile, polyurethane, polyvinylacetates, polylacticacids, starch, cellulose, polyhydroxyalkanoates, polyesters, polycaprolactone, polyvinylalcohol, polystyrene, polyethers, polycarbonates, polyamides, polyolefins, poly(acrylic acid), Carboxy Methyl Cellulose (CMC), protein based polymers, gelatin, biodegradable polymers, cotton, latex, and any combinations of these.

16. The device according to claim 1, wherein said carrier material is a hydrogel.

17. The device according to claim 1, wherein the device comprises a syringe having two separate containers, wherein a first container contains a proton donor- and a second container contains the nitric oxide eluting polymer, wherein the syringe-type device is configured to provide admixing upon administration to said site.

18. The device according to claim 1, wherein said nitric oxide eluting polymer comprises a secondary amine in a backbone of the polymer or a secondary amine as a pendant of the polymer.

19. The device according to claim 18, wherein a positive ligand is located on an atom adjacent to the secondary amine.

20. The device according to claim 1, and further comprising an absorbent agent.

21. The device according to claim 20, wherein said absorbent agent is selected from the group consisting of polyacrylate, polyethylene oxide, CMC, microcrystalline cellulose, cotton, or starch, or and any combinations thereof.

22. The device according to claim 1, and further comprising a cation stabilizing the nitric oxide eluting polymer.

23. The device according to claim 22, wherein said cation is selected from the group consisting of $Na^+$, $K^+$, $Li+$, $Be^{2+}$, $Ca^{2+}$, $Mg^{2+}$, $Ba^{2+}$, $Sr^{2+}$, and any combinations thereof.

24. The device according to claim 1, wherein treatment site is affected by a cosmetically treatable condition selected from the group consisting of chronological age, warts, dryness, loss of elasticity, hyperseborrhea, dull complexion, dilation of the pores, hair loss, age spots, wrinkles, acne, and scarring.

25. The device according to claim 1, and further comprising a cosmetic agent selected from the group consisting of a desquamating agent, a moisturizer, a depigmenting agent, a propigmenting agent, an anti-glycation agent, a 5-alphareductase inhibitor, a lysyl hydroxylase inhibitor, a prolyl hydroxylase inhibitor, an agent for stimulating the synthesis of dermal or epidermal macromolecules, an agent for preventing the degradation of dermal or epidermal macromolecules, an agent for stimulating keratinocyte proliferation and/or differentiation, a muscle relaxant, an antimicrobial agent, a tensioning agent, an anti-pollution agent, a free-radical scavenger, and any combination of these.

26. The device according to claim 1, wherein the device is configured, when in use, to deliver a dose of NO to the treatment site of between 0.001 and 5000 ppm NO.

\* \* \* \* \*